US008597636B2

(12) United States Patent
Lazarus et al.

(10) Patent No.: US 8,597,636 B2
(45) Date of Patent: Dec. 3, 2013

(54) METHOD FOR TREATING AUTOIMMUNE DISEASES AND COMPOSITIONS THEREFOR

(75) Inventors: Alan H. Lazarus, Toronto (CA); Vinayakumar Siragam, Toronto (CA); Davor Brinc, Toronto (CA); John Freedman, Toronto (CA); Andrew R. Crow, Toronto (CA); Seng Song, Toronto (CA)

(73) Assignee: Canadian Blood Services, Ottawa, Ontario (CA)

( * ) Notice: Subject to any disclaimer, the term of this patent is extended or adjusted under 35 U.S.C. 154(b) by 983 days.

(21) Appl. No.: 11/653,688

(22) Filed: Jan. 16, 2007

(65) Prior Publication Data

US 2007/0207128 A1    Sep. 6, 2007

Related U.S. Application Data

(60) Provisional application No. 60/758,541, filed on Jan. 13, 2006.

(51) Int. Cl.
| | | |
|---|---|---|
| *A01N 63/00* | (2006.01) | |
| *A61K 39/395* | (2006.01) | |
| *C07K 16/00* | (2006.01) | |

(52) U.S. Cl.
USPC ... 424/93.1; 424/93.7; 424/93.71; 424/130.1; 424/172.1; 424/173.1

(58) Field of Classification Search
None
See application file for complete search history.

(56) References Cited

U.S. PATENT DOCUMENTS

| 5,130,141 A | 7/1992 | Law |
|---|---|---|
| 6,958,241 B2 | 10/2005 | Martin |

FOREIGN PATENT DOCUMENTS

| CA | 2253058 | 2/2000 |
|---|---|---|
| WO | WO 99/03495 | 1/1999 |
| WO | WO 02/40047 | 5/2002 |
| WO | WO 02/076384 | 10/2002 |
| WO | WO/2005/094880 | 10/2005 |

OTHER PUBLICATIONS

Spisek et al. Transfusion 2006 46:55-65.*
Marjon et al. The Jounal of Immunology. (2009) 182:1397-1403.*
Shad et al. (Pediatric Drugs 2005; 7(5):325-336.*
Lim et al. European Journal of Immunology 2009. 39:1334-1343.*
Definition of syngeneic. NCI Dictionary of Cancer Terms, Apr. 7, 2010. p. 1.*
Allogeneic-definition from Merriam-Webster, Apr. 7, 2010, pp. 1-2.*
Nimmejahn et al. Immunity 24, Jan. 19-28, 2006. p. 19-28.*
Nimmerjahn et al. Nature Review Immunology 2008 8:34-47.*
Bussel, James B.; Fc Receptor Blockade and Immune Thrombocytopenic Purpura; Siminars in Hematology, vol. 37, No. 3, Jul. 2000, pp. 261-266.
Bussel, J.B.; The use of intravenous gamma-globulin in idiopathic thrombocytopenic purpura; Medline, 1989, XP002226230, Abstract, p. 1.
Ericson, S.G, et al.; Monoclonal antibody 197 (anti-FcγRI) infusion in a patient with immune thrombocytopenia purpura (ITP) results in down-modulation of FcγRI on circulating monocytes; British Journal of Haematology; vol. 92, No. 3; Mar. 1996; pp. 718-724.
Song, Seng et al.; Monoclonal IgG can ameliorate immune thrombocytopenia in a murine model of ITP: an alternative IVIG; Blood; May 1, 2003, vol. 101, No. 9 pp. 3708-3713.
Lazarus, Alan H., et al., Monoclonal antibodies which mimic the action of intravenous immunoglobulin (mIVIG) can inhibit Immune thrombocytopenia, Biosis, 2001, XP002374393, Abstract, p. 1.
European Patent Office Examination Report dated Oct. 23, 2007 for European Patent Application No. 05732213.3-2402, pp. 1-3.
Latour. Sylvain; Induction of Tumor Necrosis Factor-α Production by Mast Cells Via FcγR; The Journal of Immunology; Sep. 15, 1992; vol. 149, 2155-2162.
Akilesh, Shreeram et al.; The MHC class 1-like Fc receptor promotes humorally mediated autoimmune disease; Journal of Clinical Investigation; May 2004; vol. 113-9; 1328-1333.
De Andres, Belen et al.; Phosphoinositide Breakdown is Associated With Fc-γRII-Mediated Activation of 5'-Lipoxygenase in Murine Eosinophils; Jour. of Immunology; vol. 146; 1566-1570.
Takai, Toshiyuki; Paired immunoglobulin-like receptors and their MHC class I recognition; Immunology; 2005; 115, 433-440.
Samuelsson, Astrid et al.; Anti-inflammatory Activity of IVIG Mediated Through the Inhibitory Fc Receptor; 2001; Science 291, 484-486.
Cao, Xianhua; The Inositol 3-Phosphatase PTEN Negatively Regulates Fcγ Receptor Signaling, but Supports Toll-Like Receptor 4 Signaling in Murine Peritoneal Macrophages; Jour. of Immunology, 2004; 4851-4857.
Crow, Andrew R., at al.; IVIg-mediated amelioration of murine ITP via FcγRIIB is Independent of SHIP1, SHP-1 and Btk activity; Blood; Jul. 2003; vol. 102 No. 2; 558-560.
Crow, Andrew R., at al.; IVIg Inhibits reticuloendothelial system function and ameliorates murine passive-immune thrombocytopenia independent of anti-idiotype reactivity; British Journal of Haematology 2001, 115: 679-686.

(Continued)

*Primary Examiner* — Chun Dahle
(74) *Attorney, Agent, or Firm* — Jenkins, Wilson, Taylor & Hunt, P.A.

(57) ABSTRACT

A method of cell-based therapy for treating an autoimmune disease is disclosed. The method is directed at stimulating leukocytes and/or dendritic cells to interrupt autoimmunity in a host. The method provides a Fcγ receptor-specific complex or a complex which results in the co-crosslinking of Fcγ-chains for treating the leukocytes and/or dendritic cells which are in turn used to elicit an autoimmune interruption response in a subject with an autoimmune disease. The Fcγ receptor-specific complex and/or complex which results in the co-crosslinking of Fcγ-chains is used to treat a biological sample comprising leukocytes and/or dendritic cells from a patient, and upon reintroducing said biological sample to the patient, the pre-treated dendritic cells illicit an autoimmune interruption response in vivo.

7 Claims, 13 Drawing Sheets

(56) References Cited

OTHER PUBLICATIONS

Bruhns, Pierre et al.; Colony-Stimulating Factor-1-Dependent Macrophages Are Responsible for IVIG Protection In Antibody-Induced Autoimmune Disease; Immunity; Apr. 2003; vol. 18, 573-581.
Nimmerjahn, Falk et al.; FcγRIV: A Novel FcR with Distinct IgG Subclass Specificity; Immunity; Jul. 2005; vol. 23, 41-51.
Timms, John F.; Identification of Major Binding Proteins and Substrates for the SH2-Containing Protein Tyrosine Phosphatase SHP-1 in Macrophages; Bolecular and Cellular Biology; Jul. 1998, vol. 18, p. 2838-3850.
Binstadt, Bryce A. et al.; IgG Fc receptor polymorphisms in human disease; Implications for intravenous immunoglobulin therapy; J Allelrlgy Clin Immunol; Apr. 2003; vol. 111, No. 4; 697-703.
Daeron, Marc et al.; Murine Recombinant FcγRIII, but not FcγRII, Trigger Serotonin Release in Rat Basophilic Leukemia Cells; Jour. of Immunology; Aug. 1992; vol. 149, 1365-1373, No. 4.
Siragam, Vinayakumar et al.; Intravenous immunoglobulin ameliorates ITP via activating Fcγ receptors on dendritic cells; Nature Medicine; Jun. 2006; vol. 12, No. 6, 688-698.
Song, Seng et al.; Monoclonal IgG can ameliorate immune thrombocytopenia in a murine model of ITP; an alternative to IVIG; Blood; May 2003, vol. 101, No. 9, 3708-3713.
Kuter, David et at.; The Reciprocal Relationship of Thrombopoietin (c-Mpl Ligand) to Changes in the Platelet Mass During Busulfan-Induced Thrombocytopenia in the Rabbit; Blood, May 1995; vol. 85, No. 10, 2720-2730.
Aigner, Silke et al.; CD 24 mediates rolling of breast carcinoma cells on P-selectin; The FASEB Journal; Sep. 1998; vol. 12, 1241-1251.
Ristamaki, Raija; Serum CD44 in Malignant Lymphoma; An Association with Treatment Response; Blood; Jul. 1994; vol. 84, 238-243.
Siragam, Vinayakumar; Can antibodies with specificity for soluble antigens mimic the therapeutic effects of intravenous IgG in the treatment of autoimmune disease?; Jour. of Clinical Investigation; Jan. 2005; vol. 115 No. 1; 155-160.
Ott, Vanessa L., et al.; FcγRIIB as a potential molecular target for intravenous gamma globulin therapy; J. Allergy Clin Immunol; Oct. 2001; S95-S98.
Pecorino, Lauren; Stem Cells for Cell-Based Therapies; Jul. 2001; www.action bioscience.org/biotech/pecorino2.html, pp. 1-7.
Reddy, Vijay, *Will Dendritic Cell-Based Therapies Have a Role in Leukemia Therapy*? Invited oral presentation, Shards Cancer Center Symposium, Oct. 11-12, 2004. Gainesville, FL., http://medinfo.ufi.edu/cme/grounds/cancer/reddy/index.html. pp. 1-54.
Clynes, Raphael; Immune complexes as therapy for autoimmunity; Journal of Clinical Investigation; vol. 115-1; 25-27.
Crow et al., "The Mechanisms of Action of Intravenous Immunoglobulin and Polyclonal Anti-D Immunoglobulin in the Amelioration of Immune Thrombocytopenic Purpura: What Do We Really Know?" Transfusion Medicine Reviews. vol. 22, No. 2 pp. 103-116 (2008).
International Search Report corresponding to International Application No. PCT/CA2005/000472 dated Jul. 27, 2005.
Podolanczuk et al., "Of mice and men: an open-label pilot study for treatment of immune thrombocytopenic purpura by an inhibitor of Syk," Clinical Trials and Observations. vol. 113, No. 14 pp. 3154-3160 (2009).
Song et al., "Monoclonal antibodies that mimic the action of anti-D in the amelioration of murine ITP act by a mechanism distinct from that of IVIg," Hemostasis, Thrombosis, and Vascular Biology. vol. 105, No. 4 pp. 1546-1548 (2005).
Barratt-Boyes, S.M., and Figdor, C.G., "Current issues in delivering DCs for immunotherapy," Cytotherapy. vol. 6, No. 2 pp. 105-110 (2004).
de Fougerolles et al., "Regulation of inflammation by collagen-binding integrins α1β1 and α2β1 in models of hypersensitivity and arthritis," The Journal of Clinical investigation. vol. 105, No. 6 pp. 721-729 (2000).
Dietz et al., "Clinical-grade manufacturing of DC from CD14+ precursors: experience from phase I clinical trials in CML and malignant melanoma," Cytotherapy. vol. 6, No. 6 pp. 563-570 (2004).
Lutz et al., "An advanced culture method for generating large quantities of highly pure dendritic cells from mouse bone marrow," Journal of Immunological Methods. vol. 223 pp. 77-92 (1999).
McKenzie et al., "The Role of the Human Fc Receptor FcγRIIA in the Immune Clearance of Platelets: A Transgenic Mouse Model," The Journal of Immunology. vol. 162 pp. 4311-4318 (1999).
Motta et al., Generation of dendritic cells from CD14+ monocytes positively selected by immunomagnetic adsorption for multiple myeloma patients enrolled in a clinical trial of anti-idiotype vaccination, British Journal of Haematology. vol. 121 pp. 240-250 (2003).
Rice et al., "DC preparations for therapy," Cytotherapy. vol. 6, No. 2 pp. 99-104 (2004).
"Purified Rat Anti-Mouse CD16/CD32 (Mouse BD Fc Block™)," Technical Data Sheet. BD Pharmingen™, BD Biosciences. (2 pages).
Park-Min et al., "FcγRIII-Dependent Inhibition of Interferon-γ Responses Mediates Suppressive Effects of Intravenous Immune Globulin," Immunity. vol. 26 pp. 67-78 (2007).
Wirthmueller et al., "Signal Transduction by FcγRIII (CD16) Is Mediated through the γ Chain," J. Exp. Med. vol. 175 pp. 1381-1390 (1992).
ATCC Advanced Catalog Product Description for Product # HB-197, Oct. 25, 2012.
Huang et al., "Dendritic cells modulate platelet in IVIg-mediated amelioration of ITP in mice," Blood. vol. 116, No. 23 pp. 5002-5009 (2010).

\* cited by examiner

METHOD FOR TREATING AUTOIMMUNE DISEASES AND COMPOSITIONS THEREFOR

CROSS-REFERENCE TO RELATED APPLICATIONS

This application claims priority from U.S. Provisional application No. 60/758,541, filed Jan. 13, 2006, the entirety of which is herein incorporated by reference.

TECHNICAL FIELD

The present invention relates to a method of treating an autoimmune disease, and includes compositions for use therein. More specifically, the invention relates to a Fcγ receptor-specific complex for initiating an autoimmune interruption response by leukocytes and/or dendritic cells to interrupt an autoimmune condition in a subject. Preferably, the present invention provides a cell-based method of treating an autoimmune disease that is achieved via pre-treatment of leukocytes and/or dendritic cells with a Fcγ receptor-specific complex of the present invention.

BACKGROUND OF THE INVENTION

Autoimmune conditions and disease are becoming more prevalent in society today, as our population continues to age. Existing therapeutic regimes for treating these conditions and diseases are generally harsh and expensive. IVIg (intravenous immunoglobulin) is a currently used antibody treatment used to combat autoimmunity. Immune thrombocytopenic purpura (ITP), for example, is an autoimmune disease characterised by platelet clearance mediated by pathogenic anti-platelet antibodies. It has been previously suggested that this platelet clearance is mediated by Fc γ receptor (Fc γ R)-bearing macrophages in the reticuloendothelial system (RES). Despite its extensive clinical use in treating ITP, as well as a variety of autoimmune and inflammatory disorders, the primary functional target of IVIg and its subsequent mechanism of action remain poorly understood. Furthermore, IVIg treatments are expensive, and often illicit harsh side effects.

The present study was undertaken to investigate possible alternative treatment regimes based on the current understanding of IVIg for autoimmune disease, in general.

SUMMARY OF THE INVENTION

An object of the present invention is accordingly to provide compositions for and methods of treating autoimmune diseases and conditions.

As an aspect of the invention, there is provided a method for treating an immune thrombocytopenia or inflammatory arthritis in a mammal, the method comprising:
  a) obtaining a leukocyte sample;
  b) treating the leukocyte sample with a Fcγ receptor-specific complex or a complex which results in the co-crosslinking of Fcγ-chains; and
  c) administering the treated leukocytes to the mammal; wherein the treated leukocytes ameliorate immune thrombocytopenia or inflammatory arthritis in said mammal.

In an embodiment, the leukocyte sample is obtained by separating leukocytes from whole blood taken from the mammal and/or from a healthy mammal.

In a further embodiment, the leukocyte sample comprises dendritic cells purified from leukocytes obtained from the mammal and/or a healthy mammal.

In a yet further embodiment, the leukocyte sample comprises dendritic cells cultured from a feed stock of leukocytes obtained from the mammal and/or a healthy mammal, the dendritic cells being cultured under conditions favouring propagation of dendritic cells.

In another embodiment, the leukocyte sample comprises dendritic cells generated from CD14+ monocytes obtained from the mammal and/or a healthy mammal.

Preferably, the Fcγ receptor-specific complex is effective for inducing signaling via the Fcγ receptor.

In an embodiment of the aforesaid method, the treatment step (b) comprises treating the leukocyte sample with a Fcγ receptor-specific complex, the Fcγ receptor-specific complex being effective for inducing signaling via the Fcγ receptor. In such an embodiment, the Fcγ receptor-specific complex may comprise IVIg, anti-CD44 or a ligand or hypercrosslinking agent specific for the Fcγ receptor. In an embodiment, the ligand may comprise a soluble antibody-antigen complex, for instance, OVA+anti-OVA, or any other soluble antigen-antibody combination. The hypercrosslinking agent, on the other hand, may comprise at least one antibody to Fc receptors, for instance 2.4G2, IV.3, 3G8, or a mixture thereof. Preferably, the hypercrosslinking agent will further comprise an anti-IgG antibody.

In another embodiment, the treatment step (b) comprises treating the leukocyte sample with a complex which results in the co-crosslinking of Fcγ-chains. The complex which results in co-crosslinking of Fcγ-chains may, for instance, comprise paired immunoglobulin-like receptor-A (PIR-A). In a preferred embodiment, the complex which results in co-crosslinking of Fcγ-chains will further comprise at least one anti-IgG antibody.

As a further aspect of the invention, there is provided a pharmaceutical composition for treating an immune thrombocytopenia or inflammatory arthritis in a mammal, the composition comprising leukocytes treated with a Fcγ receptor-specific complex or a complex which results in the co-crosslinking of Fcγ-chains, and a pharmaceutically acceptable carrier.

The present invention teaches the use of primed cells for in vivo treatment of autoimmune diseases and conditions. More preferably, the present invention provides a method of treating leukocytes, such as dendritic cells for example, to provide a primed cell sample adaptable to initiate an autoimmune interruption response of the innate immune system upon delivery of these primed cells to a subject with an autoimmune disease or condition. Further provided, is a Fcγ receptor-specific complex for treating cells to illicit an autoimmune interruption response in vivo.

According to one embodiment of the present invention, there is provided a method of cell-based therapy for a mammalian subject which includes systemically administering to the subject, a therapeutically effective amount of endogenous leukocytes and/or dendritic cells pre-treated with an immune complex of the present invention, and preferably pre-treated with a Fcγ receptor-specific complex, wherein said pre-treatment illicits an autoimmune interruption response by the leukocytes and/or dendritic cells when these cells are administered to the subject.

In another embodiment, an autoimmune disease treatment regime is provided to mediate a cellular response in leukocytes, such as dendritic cells, such that platelet clearance is slowed and/or inhibited, thereby treating or ameliorating an autoimmune disease.

According to a further embodiment of the present invention, there is provided a method for treating an autoimmune disease or autoimmune condition in a patient, said method comprising:

a) modulating a Fcγ receptor and/or receptor chain pathway of a leukocyte and/or dendritic cell sample to elicit an autoimmune interruption response in said patient when said leukocyte and/or dendritic cell sample is administered thereto.

According to alternate embodiments of the invention, a method as herein provided may comprise a) pretreating said leukocyte and/or dendritic cell sample with a Fcγ-specific complex to provide a cellular programming effect in said cell sample; and b) delivering said cell sample to said patient; wherein when in vivo said autoimmune interruption response ameliorates said autoimmune disease or condition.

A further embodiment of the present invention provides a method for treating an autoimmune disease in a patient, said method comprising: a) obtaining a leukocyte sample; b) pretreating said leukocyte sample with a Fcγ receptor-specific complex to initiate Fcγ-chain dependent signalling of said leukocytes; c) delivering said leukocytes to said patient; wherein when in vivo said leukocytes ameliorate said autoimmune disease.

An additional embodiment of the present invention provides a Fcγ receptor-stimulating antibody for treating leukocytes in vitro. A Fcγ receptor-stimulating antibody of the present invention may further include a cross-linking component and stimulates said leukocytes to ameliorate autoimmunity in vivo.

In another aspect of the invention there is provided pharmaceutical compositions for treating autoimmune diseases such as arthritis and immune thrombocytopenia, for example, comprising an effective amount of an antibody complex having specificity for a Fcγ receptor. According to a further embodiment, an antibody complex of the present invention includes a cross-linking antibody, such as anti-IgG for example.

In yet another aspect of the invention, an antibody complex of the present invention may be used in the manufacture of a medicament for the treatment of an autoimmune disease.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

Figure 1:
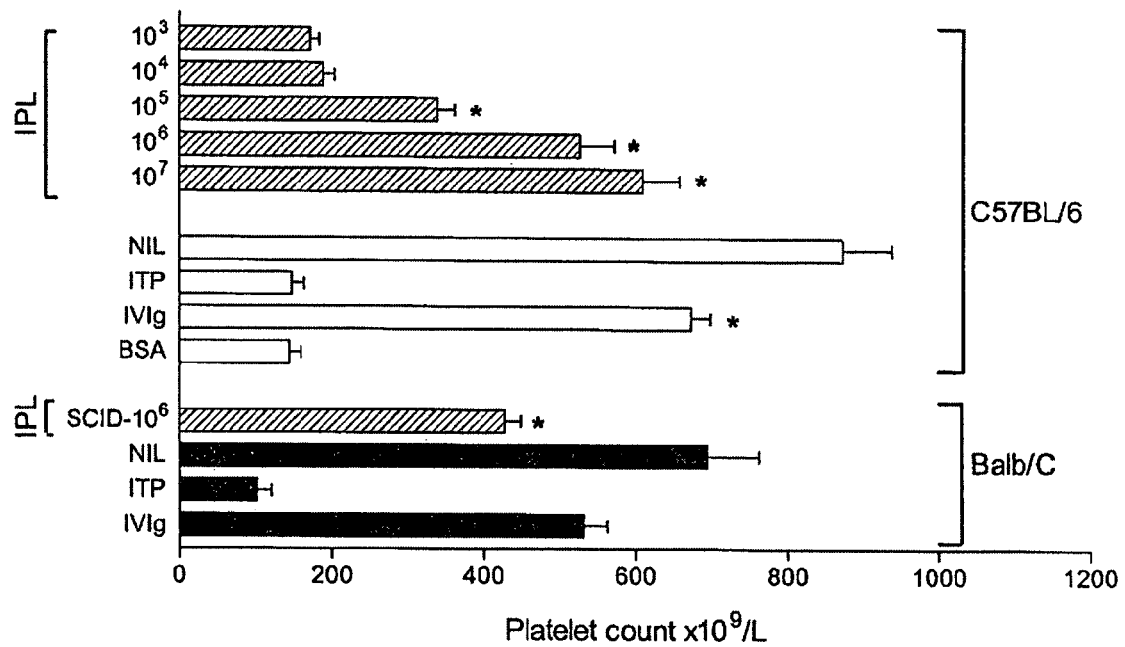
FIG. 1 is a graphical representation of the effects of intravenous treatment of mice with IVIg-primed leukocytes. C57BL/6: Splenic leukocytes from C57BL/6 mice were treated with 18 mg/ml IVIg in vitro for 30 minutes, washed and the indicated number of IVIg-primed leukocytes (IPL, $10^3$-$10^7$) injected intravenously into recipient C57BL/6 mice (hatched bars), followed 24 hours later by injection of 2 μg anti-platelet antibody. Platelet counts were performed after a further 24 hr. NIL (open bars), unmanipulated C57BL/6 mice; ITP (open bars), C57BL/6 mice injected with anti-platelet antibody only; IVIg, BSA, (open bars) C57BL/6 mice which have received standard therapy with IVIg (50 mg/mouse, intraperitoneally) or BSA (as a treatment control) followed 24 hr later by anti-platelet antibody. BALB/c: Experiments performed using BALB/c mice. SCID-$10^6$; IVIg-primed leukocytes from donor severe combined immune deficient (SCID) mice (hatched bar) treated with IVIg as described above and injected ($10^6$/mouse) intravenously into recipient BALB/c mice followed 24 hr later by injection of anti-platelet antibody. NIL, ITP, IVIg (filled bars) were as above except using BALB/c mice. The Y axis-denotes the treatments given to mice; X-axis denotes platelet counts taken 24 hours after injection with antiplatelet antibody; n=6 mice for each group from 3 independent experiments. * P<0.001 vs. ITP mice. Data are presented as mean±SEM (15-17).

Here, it is demonstrated for the first time that an autoimmune interruption response can be initiated via activating Fcγ receptor-dependent signalling in dendritic cells, in vitro followed by delivery of these cells to a subject in need thereof. In accordance with an exemplary embodiment of the present invention, the direct induction of Fcγ receptor-dependent signalling on 'initiator' leukocytes is achieved by treating the leukocyte cell sample with a Fcγ receptor-specific complex comprising an anti-FcγRIIIA antibody (2.4G2)+anti-rat IgG complex, to prompt leukocytes to ameliorate ITP upon transfer to an appropriate host. The present invention further illustrates that the autoimmune interruption response illicited by the effects of an initiator complex are not dependent on constant or long term exposure of the initiator complex itself, rather, a FcR γ chain-dependent activation of cells from the innate immune system induced by a Fcγ receptor-specific initiator complex and these cells are adoptively transferred to a host instead of traditional administration of IVIg. A Fcγ receptor-specific complex of the present invention may include a complex having specificity to elicit an activation of Fcγ chain signalling of leukocytes, such as dendritic cells, thereby bypassing the Fcγ receptor in achieving an autoimmune interruption response. According to alternate embodiments of the present invention, an immune complex of the present invention may be pre-made according to standard protocols known in the art. Alternatively, a synthetic cross-linked anti-FcγR can be made (eg. anti-FcγR prebound to protein A/G, or anti-FcγR chemically made into a multivalent complex), for example, according to the teachings of the present invention.

An autoimmune interruption response as referred to in accordance with the present invention may be otherwise referred to as an IVIg-mediated cellular programming (IMCP) effect wherein a Fcγ receptor-specific initiator complex induces a priming event in a dendritic cell sample which endows the cells with the ability to ameliorate or inhibit autoimmune disease when delivered to a subject in need thereof. This priming event may, more specifically, occur at a Fcγ receptor or alternatively, via a Fcγ chain signalling mechanism. The term IMCP is used to reference the effect of preferred antibody complexes, and more preferably Fcγ receptor-specific initiator complexes of the present invention, that employ the ability to act like IVIg in the treatment of autoimmune disease, as described further hereinbelow.

In accordance with the present invention, it is demonstrated for the first time that a Fcγ receptor-specific initiator complex can stimulate leukocytes, in vitro and upon adoptive transfer of these cells to a subject having an autoimmune condition, autoimmunity in the subject is interrupted, such as exemplified herein with the inhibition of immune thrombocytopenic purpura (ITP). In particular, a Fcγ receptor-specific initiator complex is shown to initiate dendritic cells in vitro, in a manner similar to the effects of IVIg in vivo. Surprisingly, the expression of the inhibitory Fcγ receptor (FcγRIIB) on these 'initiator' cells was not at all required for this effect. As exemplified in the following in accordance with the present invention, the direct induction of FcγR-dependent signaling on the 'initiator' leukocytes was achieved via bypassing IVIg and instead using an anti-FcγRIIIA antibody (2.4G2)+anti-rat IgG complex, to prompt the leukocytes to ameliorate ITP upon transfer to an appropriate host. In addition, bypassing IVIg using soluble immune complexes, which possess IVIg-mimetic activity in both ITP and inflammatory arthritis, also led to this adoptively transferable IVIg-effect. In addition, stimulation of cells through an FcγR-independent but Fcγ chain-dependent activation pathway (Paired Immunoglobulin-like receptor-A) also bypassed the requirement for IVIg itself.

Pre-Treated Dendritic Cells for Treatment of Autoimmune Disease

To determine if the therapeutic effects of IVIg in autoimmunity could be recapitulated by the passive transfer of IVIg-primed innate cells, we treated splenic leukocytes isolated from normal mice as well as mice with severe combined immune deficiency (SCID) with IVIg, washed the cells free of extraneous IVIg, and passively transferred these cells into normal mice followed by injection of anti-platelet antibody to induce passive immune thrombocytopenic purpura (ITP). Both normal and SCID leukocytes treated with IVIg could protect the mice from ITP indicating that IVIg-primed innate cells can fully mediate the in vivo clinical effects of IVIg (FIG. 1). Purified B cells and T cells individually subjected to IVIg also did not resolve ITP confirming that cells of the adaptive immune system do not mediate this effect (not shown).

Figure 2:
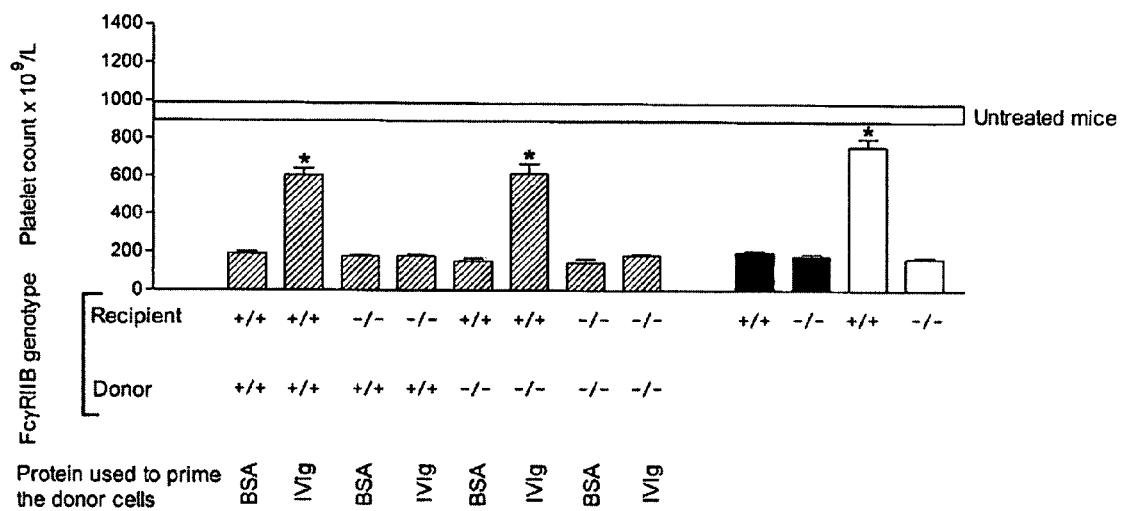
FIG. 2 is a graphical representation of the effects of inhibitory Fcγ RIIB on the IVIg-treatment of leukocytes. Splenic leukocytes from FcγRIIB$^{+/+}$ or FcγRIIB$^{-/-}$ mice were treated with 18 mg/ml IVIg or BSA in vitro for 30 minutes, washed and these leukocytes were injected ($10^6$/mouse) intravenously into recipient FcγRIIB$^{+/+}$ mice or FcγRIIB$^{-/-}$ mice (hatched bars), followed by antiplatelet antibody as in FIG. 1. The X-axis labels denote the FcγRIIB genotype of the recipient mice, the FcγRIIB genotype of the donor leukocytes, and the protein used to prime the donor leukocytes. The FcγRIIB$^{+/+}$ and FcγRIIB$^{-/-}$ genotypes are represented as +/+ or −/−, respectively. The platelet counts of untreated FcγRIIB$^{+/+}$ mice vs FcγRIIB$^{-/-}$ mice were not significantly different, the open horizontal bar (untreated mice) represents the mean platelet count ±1 SEM of FcγRIIB$^{-/-}$ mice. Mice receiving antiplatelet antibody only (solid bars) and ITP mice receiving standard IVIg therapy (open bars) are also shown. Y-axis denotes platelet counts taken 24 hours after injection with antiplatelet antibody; n=6 mice for each group from 3 independent experiments. * P<0.001 vs. ITP mice. Data are presented as mean±SEM.

It has been observed that IVIg action in the KRN×NOD (K/B×N) arthritis model may be dependent upon innate cells; specifically, colony-stimulating factor-1-dependent macrophages were shown to be pivotal as the IVIg sensor cell (1). Macrophages express the full range of standard FcγR's and it is known that IVIg's effects in both murine ITP and inflammatory arthritis are completely dependent upon the expression of the inhibitory FcγRIIB (1-4). As a result, IVIG has been speculated by some to interact with this inhibitory FcγR in the amelioration of autoimmunity and inflammation (5, 6). To determine if FcγRIIB expression is required on the IVIg 'initiator' leukocytes, we treated FcγRIIB$^{+/+}$ vs FcγRIIB$^{-/-}$ splenic leukocytes with IVIg in vitro and injected the leukocytes into recipient FcγRIIB$^{+/+}$ vs FcγRIIB$^{-/-}$ ITP mice (FIG. 2). The expression of FcγRIIB on the donor leukocytes was not at all required for the amelioration of ITP. Conversely, IVIg-primed leukocytes from either FcγRIIB$^{+/+}$ or FcγRIIB$^{-/-}$ mice only ameliorated ITP when the recipient mouse expressed the inhibitory FcγRIIB. This clearly establishes that IVIg does not require any direct interaction with FcγRIIB on the initiator leukocyte to ameliorate ITP.

Figure 3:
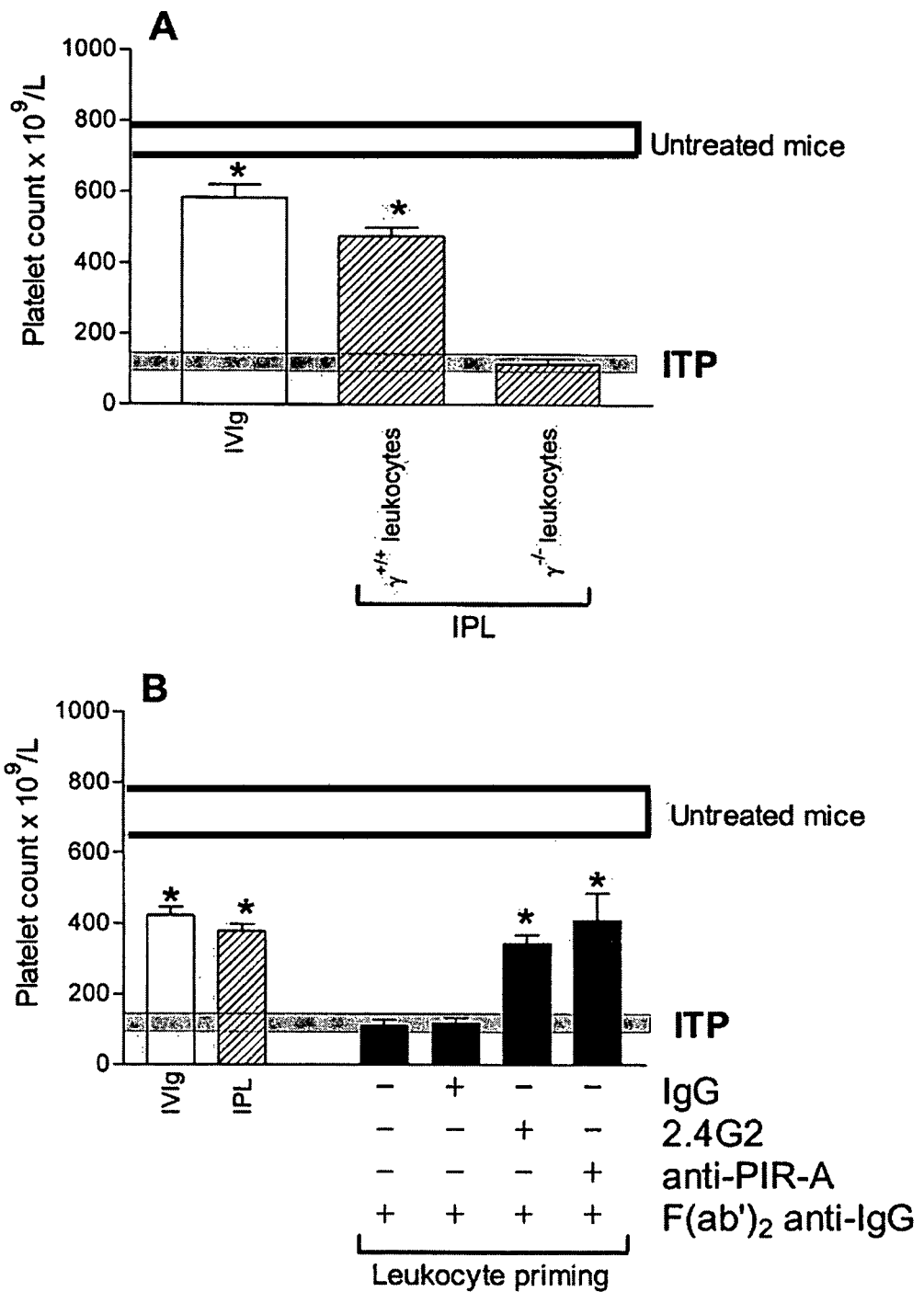
FIGS. 3A & 3B are graphical representations illustrating the role of Fcγ chain-dependent signals in ameliorating murine ITP. Panel A: C57BL/6 recipient mice were injected with IVIg (open bar) or with IVIg-primed leukocytes (IPL, $10^6$/mouse) from donor C57BL/6 (γ chain$^{+/+}$) mice or IVIg-primed leukocytes from γ chain/mice (hatched bars) followed by antiplatelet antibody at 24 hours. Panel B: C57BL/6 mice were injected with IVIg (open bar), IVIg-primed leukocytes (hatched bar), or with leukocytes pre-treated with control rat IgG, anti-FcγRIIIA (2.4G2), or anti-PIR-A (6C1) followed by (Fab')$_2$ anti-rat IgG, (filled bars). ITP (grey horizontal bar), indicates the mean platelet count (±1 SEM) of mice injected with antiplatelet antibody only. Untreated mice (open horizontal bar), indicates the mean platelet count of unmanipulated mice (±1 SEM); n=9 mice for each group from 3 independent experiments. * P<0.001 vs. ITP mice. Data are presented as mean±SEM.

To determine if IVIg effects are mediated in a manner that is dependent upon activating FcγR signals, leukocytes from mice lacking expression of the FcR γ chain were treated with IVIg and these cells passively transferred into normal mice followed by injection of anti-platelet antibody to induce ITP (FIG. 3A). IVIg-primed leukocytes from FcR γ chain deficient mice did not inhibit ITP. This finding suggests that signals from activating Fcγ receptors (FcγR's) may be primarily involved in IVIg action. To substantiate this finding, we attempted to completely by-pass the need for IVIg itself by directly inducing FcγR-dependent signalling in cells using a rat antibody directed to murine FcγRIIIA (2.4G2)+ a cross-linking antibody which induces FcγR-dependent signalling events in macrophages and other cells (7-9). Leukocytes were pre-treated with antibody 2.4G2 (ATCC Catalog No. HB-197), washed, and reacted with an F(ab')$_2$ anti-rat IgG antibody. When these cells were injected into appropriate mice, they completely recapitulated the effects of IVIg by ameliorating the murine ITP (FIG. 3B). This indicates that IVIg itself is not the only entity which can induce an IVIg-like priming effect on leukocytes to prime cells to illicit what we also refer to herein as an IVIg-mediated cellular programming (IMCP) effect. Because 2.4G2 binds FcγRIIIA as well as FcγRIIB, it is possible that the ameliorative effects observed could be due to cross-linking FcγRIIB or co-cross-linking FcγRIIB with FcγRIIIA. To address this possibility, we evaluated the 2.4G2 passive-transfer effects using cells isolated from mice lacking the inhibitory FcγRIIB; cells from FcγRIIB$^{-/-}$ mice reacted with antibody 2.4G2+F(ab')$_2$ anti-IgG mediated passively-transferred amelioration of ITP (not shown) indicating that the cross-linking or co-cross-linking of FcγRIIB on the initiator cells is not involved in mediating this effect.

To independently verify that Fc γ chain-dependent signaling plays a pivitol role in mediating the effects of IVIg, we sought to induce γ chain-dependent signaling in a manner which is independent of the presence of the various FcγR's themselves. A potential molecule which is expressed on cells of the innate immune system and induces Fc γ chain-dependent cellular activation is the paired immunoglobulin-like receptor-A (PIR-A). PIR-A (and it's inhibitory counterpart, PIR-B) act as physiological receptors for the major histocompatibility complex (MHC) class I molecules (recently reviewed in (10)). PIR-A acts as an activating receptor by virtue of its immunoreceptor tyrosine-based activation motif (ITAM) which associates with the Fc γ chain and induces cellular activation. Since PIR-A is not an immunoglobulin receptor, we sought to activate Fc γ chain-dependent signaling independent of the contribution of FcγR's by cross-linking PIR-A on leukocytes using antibody 6C1 in combination with F(ab')$_2$ anti-IgG to determine if the passive transfer of these cells could mediate an IVIg-like effect. Leukocytes treated with antibody 6C1 in combination with F(ab')$_2$ anti-IgG ameliorated the murine ITP (FIG. 3B). This indicates that the direct stimulation of Fc γ chain-dependent signalling in leukocytes was sufficient to induce amelioration of ITP. Although the above regime would also be expected to engage PIR-B which drives negative signaling, PIR-B preferentially associates with SHP-1 in murine macrophages (11) and we have previously observed that IVIg-mediated amelioration of murine ITP occurs in a SHP-1-independent manner (3).

Figure 4:
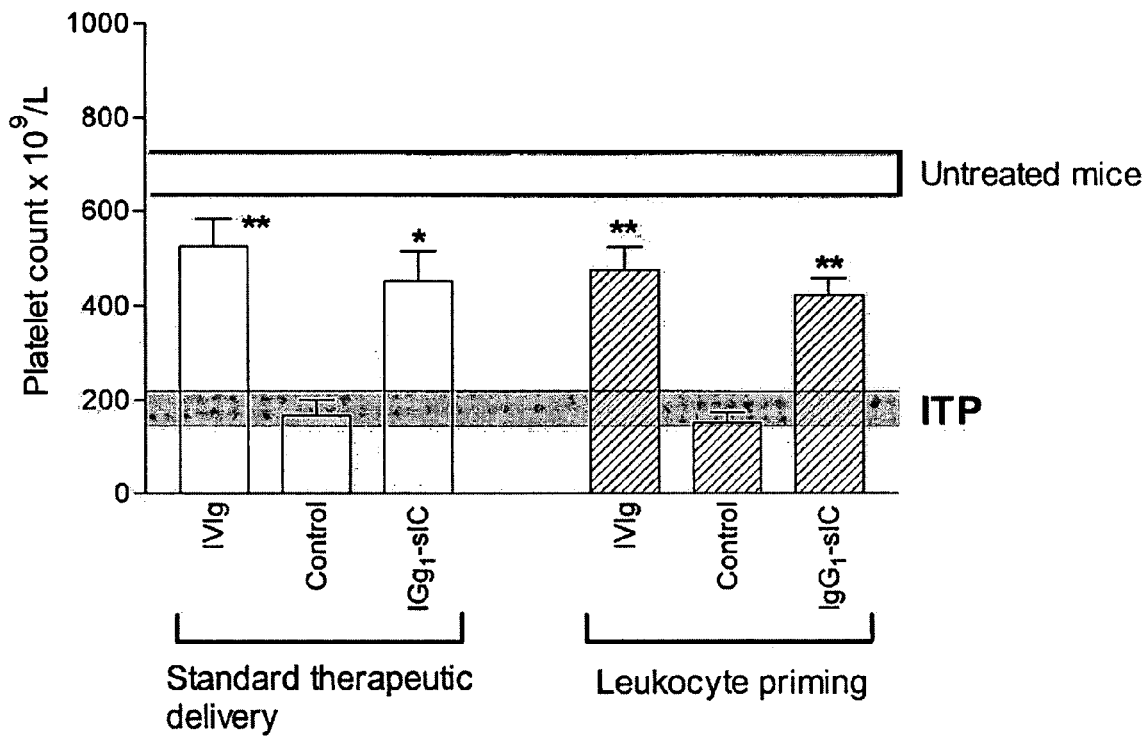
FIG. 4 is a graphical representation illustrating the use of soluble immune complexes for leukocyte priming, according to an embodiment of the present invention. Standard therapeutic delivery (open bars): C57BL/6 mice were treated with an intraperitoneal injection of IVIg (IVIg) by as in FIG. 1, an intravenous injection of control mouse IgG+OVA (Control), or an intravenous injection of soluble immune complexes consisting of OVA that had been pre-incubated with an IgG$_1$ monoclonal anti-OVA antibody (IgG$_1$-sIC). The above mice then received antiplatelet antibody at 24 hours. Leukocyte priming (hatched bars): Leukocytes from C57BL/6 mice were pretreated with IVIg (IVIg), control mouse IgG+OVA (Control), or IgG$_1$ soluble immune complexes (IgG$_1$-sIC), washed, and the cells injected into recipient mice as in FIG. 1. Mice were injected with antiplatelet antibody after 24 hours as in FIG. 1. ITP (grey horizontal bar), indicates the mean platelet count (±1 SEM) of mice injected with antiplatelet antibody only. Untreated mice (open horizontal bar), indicates the mean platelet count of unmanipulated mice (±1 SEM) n=6 mice for each group from 2-independent experiments. * P<0.001, **P<0.01 vs ITP mice. Data are presented as mean±SEM.

A new FcγR has recently been discovered (FcγRIV) which utilizes FcR γ chain-dependent signalling (12) and could be a pivotal FcγR involved in IVIg action. We have recently determined that IVIg can be replaced with either polyclonal or monoclonal antibodies that form low molecular weight immune complexes and these antibodies ameliorate both ITP and inflammatory arthritis (13). These antibodies (13), like IVIg (2, 13) do not require complement to mediate their therapeutic effects and can ameliorate ITP at a 3 log fold lower dose than IVIg (2, 13) suggesting that IVIg activity may be associated with the formation of small immune complexes (14). Because FcγRIV does not bind to murine IgG$_1$ subclass antibodies (12), we assessed the ability of an immune complex formed with a monoclonal IgG$_1$ antibody, again, by-passing IVIg activity, in mediating passively-transferred amelioration of ITP. Leukocytes were treated with ovalbumin prebound with a monoclonal anti-ovalbumin antibody (reacted in a 67:1 molar (OVA:IgG) molar ratio, to favour the formation of a monovalent immune complex) and observed that these soluble IgG$_1$-immune complexes also stimulated passively-transferred amelioration of ITP (FIG. 4). This again indicates that IVIg itself is not the only entity which can induce an IVIg-like-primed leukocyte effect.

Role of Fcγ Chain Signalling in Illiciting IMCP Effect in Dendritic Cells

Figure 5:
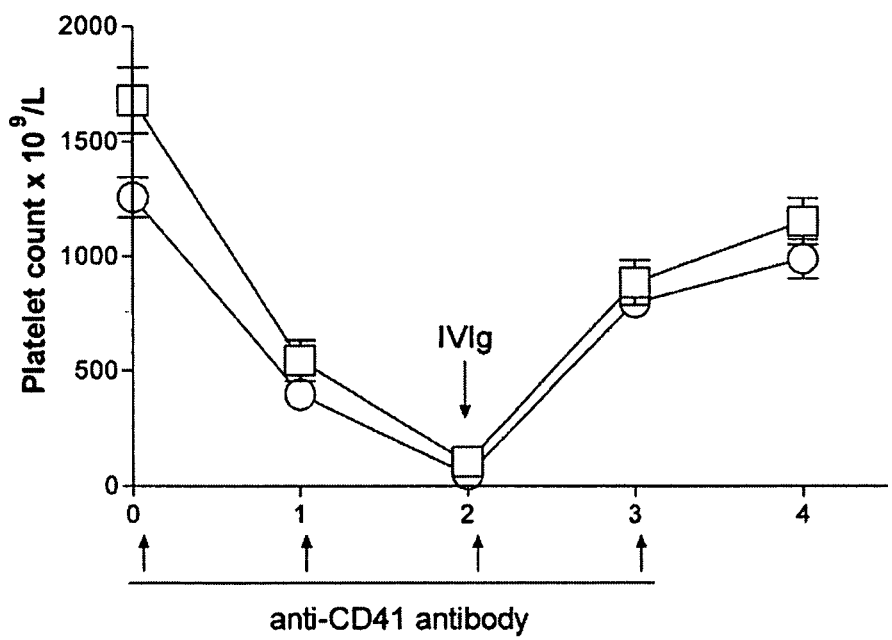
FIG. 5 is a graphical representation illustrating the role of IVIg in ameliorating thrombocytopenia in mice where endogenous murine Fcγ chain (the major signaling component linked to other activating Fcγ receptors (FcγRI, FcγRIII FcγRIV) which transmit activation signals from the crosslinked or preferably hyper-crosslinked FcγR to the cell) has been replaced by human Fcγ RIIA. Fcγ RIIA does not utilize or require the Fcγ chain to transmit signals to the cell as Fcγ RIIA contains an ITAM (Immune tyrosine-based activation motif) sequence which performs the equivalent signaling function of the Fcγ chain.

FIG. 5 illustrates the ability of IVIg to ameliorate thrombocytopenia in mice where the endogenous murine Fcγ chain has been replaced by human FcγRIIA. Female C57BL/6 mice (0, The Jackson Laboratory, Bar Harbor, Me.), or mice genetically deficient for the Fcγ chain and expressing the transgene for the human FcγRIIA (□, Fcγ$^{-/-}$ hFcγRIIA$^{+/+}$, McKenzie et. al, J Immunol 1999; 162:4311-4318) were bled daily on days 0-4 and platelets were enumerated by flow cytometry as previously described (Siragam et. al, J Exp Med 2005; 115: 155-160). Immediately following the bleeds on days 0-3 (upward arrow), mice were injected intraperitoneally with 2 μg anti-CD41 antibody (clone MWReg30, Pharmingen, Mississauga, ON) to induce thrombocytopenia. On day 2 (downward arrow), all mice received an intraperitoneal injection of 50 mg IVIg (5% Gamimune, Bayer Inc, Elkhart, Ind.). The x-axis denotes the duration of the experiment in days; the y-axis denotes platelet count. n=6 mice for each group. Fcγ$^{-/-}$, hFcγRIIA$^{-/-}$ (double negative) mice do not develop thrombocytopenia when injected with anti-CD41 (not shown).

Since Fcγ RIIA has its own ITAM signalling sequence and can fully function in the absence of the Fcγ chain, these data indicate that IVIG-mediated reversal of thrombocytopenia (by priming of leukocytes) does not require the specific expression of the Fcγ chain but can occur via the stimulation of an equivalent (activating) Fcγ signalling pathway.

Dendritic Cells as Target for Illiciting an Autoimmune Interruption Response

Figure 6:
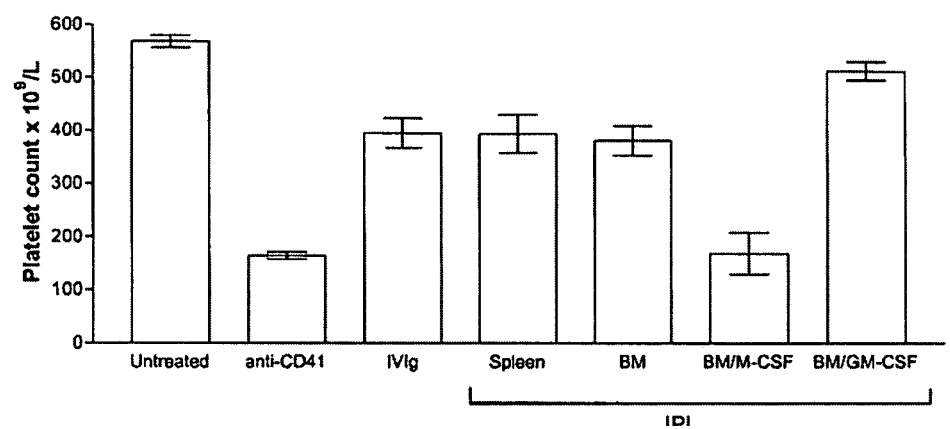
FIG. 6 is a graphical representation illustrating that IVIg-primed bone-marrow derived dendritic cells can inhibit immune thrombocytopenia. C57BL/6 mice were injected i.p. with 50 mg IVIg (Column 3) or injected with $10^6$ of the following: C57BL/6 erythrocyte-depleted splenic cells that had been primed with 18 mg/mL IVIg in vitro for 30 min, washed and injected i.v. ($10^6$/mouse) into the tail vein of recipient mice as described in detail in the Materials&Methods section (Column 4); washed IVIg-primed erythrocyte-depleted bone marrow cells (Column 5); washed IVIg-primed erythrocyte-depleted bone marrow cells that had been cultured in complete RPMI-1640 medium (RPMI-1640 supplemented with 10% fetal calf serum, 100 U/mL penicillin, 100 mg/mL streptomycin, 2 mM L-glutamine) with 50 ng/mL mouse recombinant Macrophage Colony Stimulating Factor (rM-CSF, R&D Systems, Minneapolis, Minn.) for 10 days (Column 6); washed IVIg-primed erythrocyte-depleted bone marrow cells that had been cultured in complete RPMI-1640 with 20 ng/mL mouse recombinant Granulocyte Macrophage Colony Stimulating Factor (rGM-CSF, R&D Systems, Minneapolis, Minn.) for 10 days (Column 7). Twenty-four hr later, all mice except those in Column 1 (unmanipulated mice) received an i.p. injection of 2 μg anti-CD41 antibody. After another 24 hr, all mice were bled for platelet enumeration by flow cytometry, as described in detail in the Materials&Methods section. Cultures with rGM-CSF were done according to the method of Lutz et. al, J Immunol Meth 1999; 223:77-92 (10 day maturation protocol). The rM-CSF culture followed the same 10 day culture protocol, replacing 20 ng/mL rGM-CSF with 50 ng/mL rM-CSF. n=6 mice for each group, 2 experiments of 3 mice each. Data are expressed as mean±S.E.M.

FIG. 6 illustrates the ability of IVIg-primed bone marrow derived dendritic cells to inhibit immune thrombocytopenia. According to this embodiment of the present invention, C57BL/6 mice were injected i.p. with 50 mg IVIg (Column 3) or injected with 106 of the following: C57BL/6 erythrocyte-depleted splenic cells that had been primed with 18 mg/mL IVIg in vitro for 30 min, washed and injected i.v. (10$^6$/mouse) into the tail vein of recipient mice as described in detail in the Examples (Column 4); washed IVIg-primed erythrocyte-depleted bone marrow cells (Column 5); washed IVIg-primed erythrocyte-depleted bone marrow cells that had been cultured in complete RPMI-1640 medium (RPMI-1640 supplemented with 10% fetal calf serum, 100 U/mL penicillin, 100 □g/mL streptomycin, 2 mM L-glutamine) with 50 ng/mL mouse recombinant Macrophage Colony Stimulating Factor (rM-CSF, R&D Systems, Minneapolis, Minn.) for 10 days (Column 6); washed IVIg-primed erythrocyte-depleted bone marrow cells that had been cultured in complete RPMI-1640 with 20 ng/mL mouse recombinant Granulocyte Macrophage Colony Stimulating Factor (rGM-CSF, R&D Systems, Minneapolis, Minn.) for 10 days (Column 7). Twenty-four hr later, all mice except those in Column 1 (unmanipulated mice) received an i.p. injection of 2 □g anti-CD41 antibody. After another 24 hr, all mice were bled for platelet enumeration by flow cytometry, as described in detail in the Materials & Methods section. Cultures with rGM-CSF were done according to the method of Lutz et. al, J Immunol Meth 1999; 223:77-92 (10 day maturation protocol). The rM-CSF culture followed the same 10 day culture protocol, replacing 20 ng/mL rGM-CSF with 50 ng/mL rM-CSF. n=6 mice for each group, 2 experiments of 3 mice each. Data are expressed as mean±S.E.M.

Use of Pretreated Dendritic Cells to Illicit an Autoimmune Interruption Response In Vivo As indicated hereinabove, an embodiment of the present invention provides a cell based therapy for use in treating autoimmune diseases and conditions. Cellular therapies of the present invention may employ an immune complex capable of inducing Fcγ R chain dependent signalling of a dendritic cell sample, including but not limited to IVIg. Techniques and procedures relating to the preparations and administration of immune complexes of the present invention may be conducted in accordance with procedures as well known in the art, and as exemplified in the teachings of Cellular Therapy—A Physician's Handbook, 1$^{st}$ Edition 2004, available through the American Society for Blood and Marrow Transplantation, the content of which is herein incorporated by reference. Cellular therapy protocols of the present invention would be preferably provided to replace current direct IVIg and IVIg mimetic administration to a patient. According to a preferred embodiment of the present invention, a more specific stimulus of the positive effects of an IMCP effect is expected, versus direct injection of IVIg itself. According to this embodiment, a 3 log fold lower dose of IVIg or IVIg mimetics is required as a small volume of dendritic cells are pretreated rather than direct administration thereof to a patient.

According to an exemplary protocol of an embodiment of the present invention, blood is removed from a patient (or a healthy matched blood donor) using vacutainer tubes containing an anticoagulant (between 1-5 large 10 ml draw tubes). In the case where the disease is more severe, a full unit of blood (into a standard blood donation bag) may be withdrawn from the individual. Although the blood can be treated without the need to purify the leukocytes, the leukocyte fraction of the blood may be isolated using a standard approach such as density medium (ficoll hypaque, sp gr 1.077 or an equivalent percoll density gradient) or centrifugal elutriation (leukopheresis). The isolated leukocytes (peripheral blood mononuclear cells) are then washed and resuspended in a medium compatible with cells (eg RPMI-1640) at an approximate concentration of 10$^7$ cells/ml of medium. The leukocytes are then incubated with a Fcγ receptor-initiator complex (eg. IVIg, or, a soluble immune complex prepared as described in Siragam et al. (2005)) or an anti-human FcγR specific antibody (eg. IV.3 or 3G8), or, anti-PIR-A, or, an anti-Fcγ chain specific antibody, for example, followed by a second cross-linking antibody (eg anti-IgG) to induce cell signalling in the dendritic cells. Alternatively, a chemical agent which activates Fcγ receptor-initiator complex signalling (eg. a chemical activator of syk tyrosine kinase signaling) can also be used to induce Fcγ receptor-downstream cell signalling in the dendritic cells. The cells are then allowed to interact with the Fcγ receptor-initiator complex at 37° C. for 30 minutes. The cells may then be washed in medium and prepared for injection into the patient by an intravenous injection.

As an alternative to the direct use of leukocytes, it may be preferred that dendritic cells be cultured in dendritic cell growth medium to provide a more effective treatment. In this scenario, the leukocytes (or purified CD14$^+$ monocytes, or purified CD11c$^+$ cells, or purified CD34$^+$ cells) would be cultured in a typical dendritic cell growth media prior to use in step 3, above. eg of references for dendritic cell growth in culture include (Rice A M et al., Cytotherapy vol 6 (2) pp 99-104; Barratt-Boyes S M & Figdor C G, Cytotherapy vol 6 (2) pp 105-110; Dietz A B et al., Cytotherapy vol 6 (6) pp 563-570; Motta M R et al., Br J. Haematol. 2003 April; 121(2):240-50.)

Conclusions

In summary, these data suggest that IVIg induces FcγR-dependent signalling in innate IVIg sensor cells and that the effects of IVIg are not dependent upon long term exposure of the IVIg itself, rather, a Fcγ receptor-specific complex can prime cells to illicit a IMCP effect and these cells can be adoptively transferred to a host to effect an autoimmune interruption response therein. Thus, the cell-based therapy of the present invention provides an alternative treatment to the intravenous administration of IVIg.

The following examples illustrate methods of preparing, characterizing and/or using embodiments of the present invention and are in no way intended to limit the scope thereof.

EXAMPLES

Example I

Material and Methods
K/BxN Serum-Induced Arthritis and Arthritis Scoring:

For induction of arthritis, mice were given a single intraperitoneal injection of 600 µl of diluted serum (diluted to 50% strength with PBS) as previously described by Akilesh et al. (Akilesh, S., Petkova, S., Sproule, T. J., Shaffer, D. J., Christianson, G. J., and Roopenian, D. 2004. The MHC class I-like Fc receptor promotes humorally mediated autoimmune disease. *J Clin Invest* 113:1328-1333).

An additional control group of mice were injected with only PBS instead of K/BxN serum. Ankle width was measured laterally across the joint with a caliper (Samona International, Canada). Arthritis was also clinically scored daily by an independent blinded observer. Each paw was scored as follows: 0, [unaffected], 1 [slight swelling], 2 [moderate swelling], 3 [severe swelling involving the entire paw (foot, digits, ankle)], and the overall score was calculated as the sum of individual scores for each paw as described by de Fougerolles et al. (de Fougerolles, A. R., Sprague, A. G., Nickerson-Nutter, C. L., Chi-Rosso, G., Rennert, P. D., Gardner, H., Gotwals, P. J., Lobb, R. R., and Koteliansky, V. E. 2000. Regulation of inflammation by collagen-binding integrins alpha1beta1 and alpha2beta1 in models of hypersensitivity and arthritis. J Clin Invest 105:721-729). Mice injected with anti-albumin or the IgG control received 1 mg of IgG intravenously in 200 µl PBS four hours prior to the induction of arthritis. Mice injected with IVIg received 50 mg of IVIg by an intraperitoneal injection four hours prior to the induction of arthritis.

Figure 7:
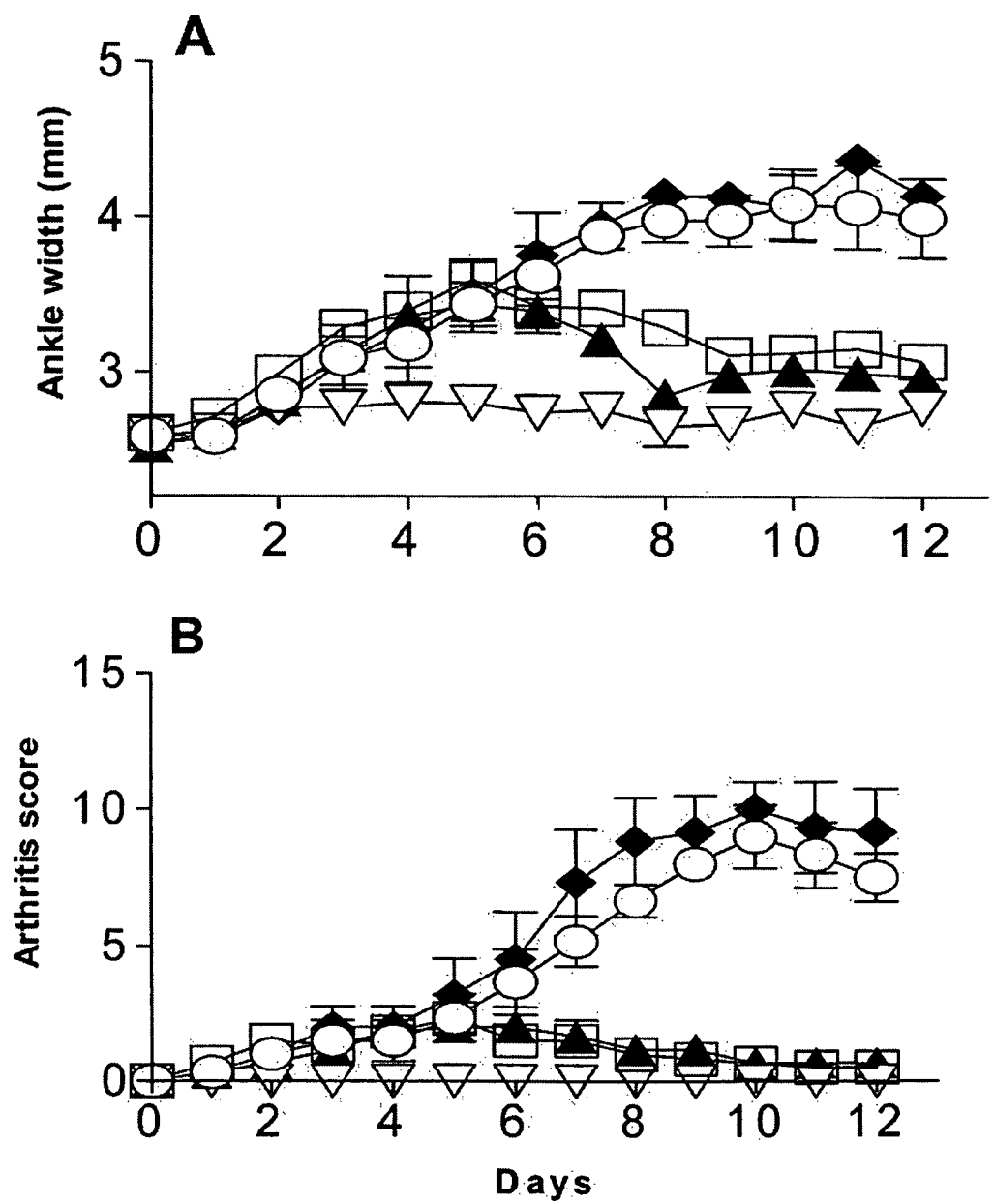
FIGS. 7A and 7B are graphical plots illustrating that antibodies to albumin ameliorate K/BxN serum-induced inflammatory arthritis.

IgG Reactive with a Soluble Antigen can Ameliorate Arthritis:

To further evaluate the therapeutic role of antibodies directed to soluble antigens in the K/BxN serum-induced arthritis model, C57BL/6 mice were injected with 50 mg IVIg, 1 mg anti-albumin, 1 mg non-immune IgG, or nothing 4 hours prior to receiving K/BxN serum. An additional control group of mice were injected with only PBS in place of the K/BxN serum. Mice that received K/BxN serum alone, or K/BxN serum+non-immune IgG, developed joint swelling (FIGS. 7A and B). As shown in FIGS. 7A & 7B, antibodies to albumin ameliorate K/BxN serum-induced inflammatory arthritis. (A) Ankle width and (B) overall arthritis score following K/BxN serum-induced arthritis. C57BL/6 mice were injected on day 0 with K/BxN serum (O), IVIg+K/BxN serum (□), anti-albumin+K/BxN serum (▲), Non-immune IgG+K/BxN serum (♦), or treated with only PBS in place of K/BxN serum (∇). Data are represented as the mean±SEM; n=3 mice for each group.

IVIg and the anti-albumin treatment significantly ameliorated the arthritis as assessed by ankle width measurements as well as by clinical score as compared to mice that received K/BxN serum or K/BxN serum plus treatment with non-immune IgG (FIGS. 7A and 7B).

Example II

An Underlying Mechanism of Action for IMCP Effect

Our further investigation has also revealed surprising evidence for the mechanism of action of the treatment regimes as herein disclosed. In particular, we have established that antibody treatment regimes such as IVIg, a monoclonal antibody to CD44 antigen and anti-soluble immune complex antibodies (in the presence of the antigen) work to ameliorate autoimmune disease via an antibody-mediated cellular programming mechanism, otherwise herein referred to as IMCP, of non-B and non-T cell leukocytes. In particular, we show that IVIg, monoclonal antibody to CD44 antigen (FIG. 8, Ab1) and anti-soluble immune complex antibodies (in the presence of the antigen) can bind to leukocytes in vitro and upon transfer in vivo, can ameliorate ITP, for example. More specifically, IVIg, a monoclonal antibody to the CD44 antigen, and anti-soluble immune complex antibodies (in the presence of the antigen) ameliorate autoimmune disease by interacting with a non-B cell non-T cell leukocyte which then, upon transfer to a host with an autoimmune disease, ameliorates disease activity. We have found that the leukocyte which mediates these clinical effects co-purifies with cells, including a subset of intestinal epithelial lymphocytes and a subset of activated T-cells, expressing the CD11c cell surface antigen, a surface marker expressed on most dendritic cells [data not shown]. Thus, a novel mechanism of action for IVIg and IVIg-like treatment regimes for autoimmune disease is herein provided.

Figure 10:
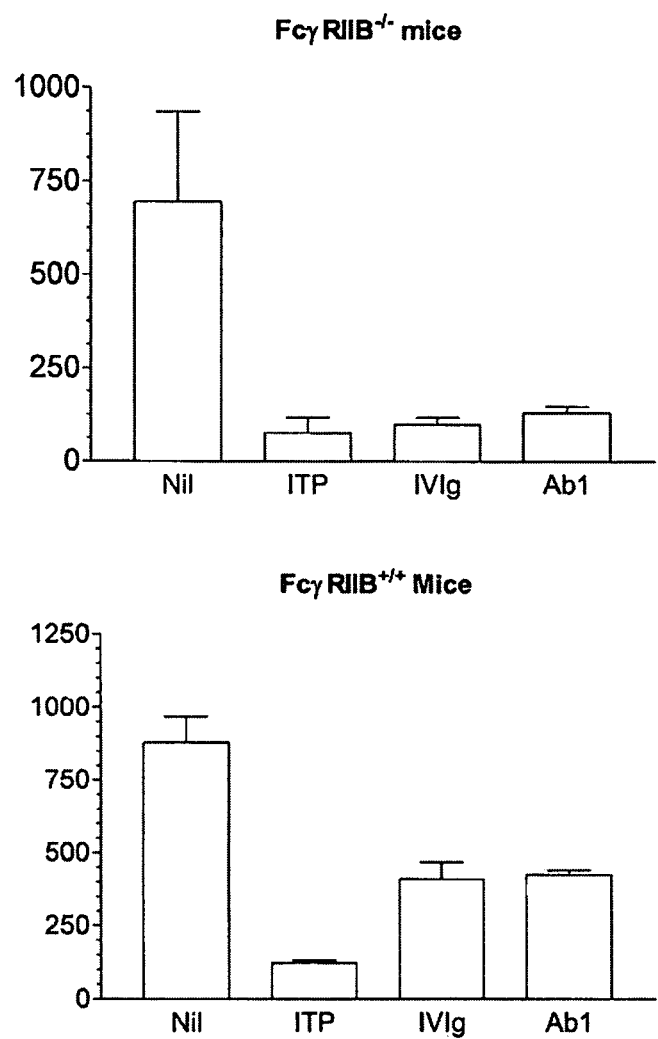
FIG. 10 is a graphical representation illustrating that anti-CD44 does not inhibit immune thrombocytopenia in Fcγ RIIb-deficient mice.

Furthermore, a common linking factor is established in that the expression of Fcγ RIIB inhibitory receptor on cells is shown in the treatment regimes for anti-CD44 (FIG. 10) and antibodies directed to soluble antigens (not shown), as has been previously established for IVIg, thus providing evidence that a common mode of action is the basis for the treatment regimes of the present invention. Having established a common mechanism of action with IVIg, anti-CD44 antibody, we believe that an antibody for a soluble antigen, in accordance with the present invention, will have a similar therapeutic effect as IVIg or anti-CD44 antibody, in the treatment and/or amelioration of a plurality of autoimmune diseases. Accordingly, the embodiments of the present invention may be extended to provide beneficial treatment regimes for the prevention and/or treatment of other autoimmune diseases.

Materials and Methods
Mice:

CD1 mice (female 6-10 wk of age) and severe combined immune deficient (SCID) virgin mice (female 6 to 8 weeks of age) were purchased from Charles River Laboratories (Montreal, PQ, Canada). C57BL/6, BALB/c, and FcγRIIB$^{-/-}$ mice were (female 8 to 12 weeks of age) were from the Jackson Laboratory (Bar Harbor, Me.).

Reagents:

The monoclonal antibody specific for integrin αIIb (rat IgG$_{1κ}$, clone MWReg 30) was purchased from BD Pharmingen (Mississauga, ON). Bovine serum albumin (BSA) was purchased from Sigma (Oakville, ON, Canada). The IVIg (Gamimune N, 10%) was from Bayer (Elkhart, Ind.). To neutralize the pH of the IVIg (in some experiments), both IVIg and BSA were dialysed against phosphate buffered saline (PBS) (pH 7.2) in 1:200 ratio for 18 hours at 4° C. using 12-14 kDa cutoff dialysis tubing (Spectrum Laboratories Inc, Rancho Dominguez, Calif.) under sterile conditions. Microdispenser tubes (250 µL) for blood collection were from VWR. Complete RPMI-1640 was RPMI-1640 medium (Sigma, Oakville, ON, Canada) supplemented with 10% heat-inactivated fetal calf serum, 80 µg/ml streptomycin sulphate, 0.2 µg/ml amphotericin B, 80 U/ml penicillin G and 1.6 mM L-glutamine.

IVIg-Mediated Cellular Programming (IMCP):
Preparation of IMCP Blood:

Blood (400 µl, or as otherwise indicated) was collected in sterile PBS containing 1% EDTA (PBS/EDTA), washed and the cell pellets resuspended in 25 mg/ml of IVIg or BSA in PBS/EDTA. After incubation for 20 min (or as otherwise indicated) at 37° C. in a shaking incubator, the cells were washed 2× in Ca++ and Mg++ free PBS, resuspended in saline and immediately injected back into the original mice. For preparation of WBC-reduced blood cells, the collected blood was first centrifuged at 900×g for 5 min at 4° C., the plasma and buffy coat fractions were discarded. The cell pellets were washed 3× in PBS and resuspended in 25 mg/ml of IVIg or BSA as described above.

Preparation of IMCP Splenic Cells:

Spleens from normal mice were removed, mechanically disrupted in 5 ml of complete RPMI-1640 medium, and then filtered through 70-µm nylon mesh strainer. Erythrocytes were lysed using 0.15 M $NH_4Cl$, 10 mM $KHCO_3$, 0.1 mM $Na_2EDTA$ (ACK) lysis buffer and washed 2× in RPMI-1640. The cells ($1.4 \times 10^6$/ml) were incubated with 18 mg/ml dialyzed IVIg (IMCP) or BSA (IMCP-control), or the indicated concentration (x/ml) of anti-CD 44 (Antibody clone KM-114), or with 1 mg of ovalbumin that was pretreated with 50 ug monoclonal anti-ovalbumin (Clone OVA-14, antibody subclass IgG1, From Sigma), or 1 mg of ovalbumin that was pretreated with 50 ug normal mouse IgG (Catalogue #10400, from Caltag) for 30 min at 37° C. in RPMI-1640. The cells were then washed 2× in RPMI-1640, resuspended to $5 \times 10^6$/ml and injected (200 µl) into the tail vein of recipient mice.

Fixation:

Pre-fixed cells: splenic leukocytes ($2.5 \times 10^6$/ml) were fixed in 1% paraformaldehyde in PBS for 10 minutes, washed 2× in PBS and then incubated with IVIg or BSA for 30 min as described above.

Post-fixed cells: splenic leukocytes were first incubated with IVIg or BSA for 30 min as described above, washed 2× in PBS and then fixed in 1% paraformaldehyde in PBS. The cells were then washed 2× in PBS, resuspended at $5 \times 10^6$/ml and injected (200 µl) into the tail vein of recipient mice.

Radiation:

Splenic leukocytes ($5 \times 10^6$/ml) were irradiated (2500 rads) using cell irradiator (γ source, Cs-137) and then incubated with IVIg or BSA as described above.

Induction and Treatment of ITP:

For the administration of IVIg, BSA, or IMPC-cells, mice were first injected intraperitoneally with 50 mg of IVIg, BSA (~equivalent to 2 g/kg body weight), IMPC cells, or control-IMCP cells. After 24 hrs, mice were rendered thrombocytopenic by the intraperitoneal injection of 2 µg anti-CD41 (anti-integrin αIIb) antibody in 200 µL PBS. Twenty-four hours later, mice were bled by the saphenous vein and the platelets were counted on a flow rate-calibrated FACScan flow cytometer (Becton Dickinson) as previously described in detail (Br. J. Haematol. 115:679-686, 2001; Blood. 101: 708-3713, 2003).

T Cell Purification:

T cells were purified from spleens by magnetic separation using a T cell negative selection kit (StemCell Technologies, Vancouver, BC) according to manufacturer's instructions. Briefly, splenocytes were prepared in Ca++ and Mg++ free PBS containing 2% heat-inactivated fetal calf serum and 5% normal rat serum at 108 nucleated cells/mL. Splenocytes were then incubated with T cell negative selection cocktail (containing antibodies to CD11b, CD45R, Ly-6G(Gr-1), TER 119) at 20 µl/mL, followed by biotin selection cocktail at 100 µl/mL, and magnetic nanoparticles at 100 µl/mL. All incubations were done for 15 min at 4oC. The recovered cells were stained with anti-CD3-FITC (10 µg/mL) and anti-CD19-PE (4 µg/mL) for 30 min at 4oC, washed, and analyzed by a FACScan flow cytometer. The recovered cells were routinely >90% CD3+ and <1% CD19+.

B Cell Purification:

B cells were purified from the spleen by magnetic separation using a B cell negative selection kit (StemCell Technologies, Vancouver, BC) according to manufacturer's instructions. Briefly, splenocytes were prepared in Ca++ and Mg++ free PBS containing 2% heat-inactivated fetal calf serum and 5% normal rat serum at 108 nucleated cells/mL. Splenocytes were then incubated with mouse FcR blocker (anti-CD16/32) at 10 µl/mL, B cell negative selection cocktail (containing antibodies to CD4, CD8, CD11b, Ly-6G(Gr-1), TER 119) at 20 µl/mL, followed by biotin selection cocktail at 100 µl/mL, and magnetic nanoparticles at 100 µl/mL. All incubations were done for 15 min at 4oC. The recovered cells were stained with anti-CD3-FITC (10 µg/mL) and anti-CD19-PE (4 µg/mL) for 30 min at 4oC, washed, and analyzed by FACScan flow cytometer. The recovered cells were routinely >80% CD19+ and 10% CD3+.

Results

Figure 11:
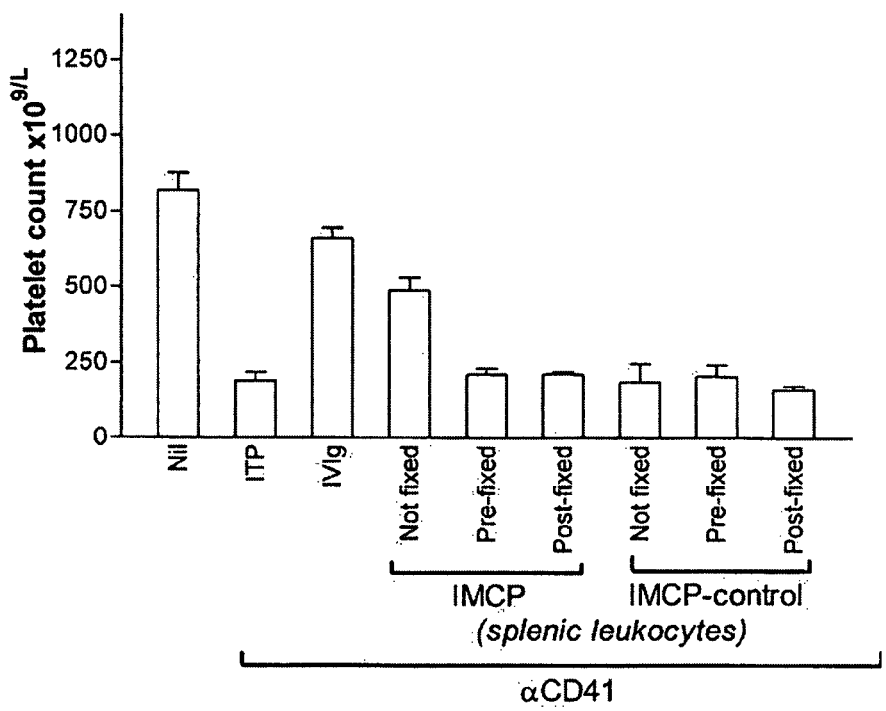
FIG. 11 is a graphical representation illustrating that IMCP is a fixation-sensitive process.
Figure 12:
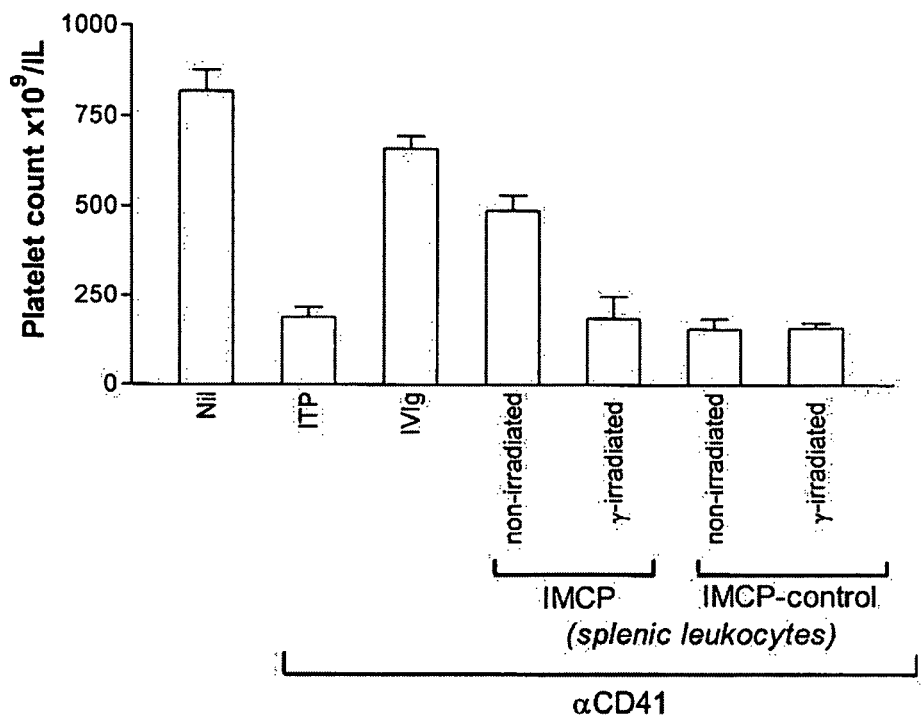
FIG. 12 is a graphical representation illustrating that IMCP is a radiation-sensitive process.

We found that leukocytes can be treated with IVIg in vitro, washed free of unbound IVIg, and when as little as $10^6$ of these cells are injected into a mouse, an IVIg-like effect is observed (ie. rapid reversal of the autoimmune disease symptom, in ITP, thrombocytopenia). This effect is specifically observed with blood or splenic leukocytes, but not red blood cells. The leukocytes must also be biologically active (ie γ irradiated or paraformaldehyde fixed leukocytes do not work, FIGS. 12 and 11, respectively) indicating that simple passive transfer of the IVIg is not the mode of action. B and T cells are not required for this clinical effect of IVIg. Thus, we have strong experimental evidence that the antibody-based treatment regimes of the present invention, induce a priming event in innate leukocytes which endows leukocytes with the ability to ameliorate or inhibit autoimmune disease, specifically in ITP, thrombocytopenia, or in inflammatory arthritis, joint inflammation. We call this effect "IVIg-mediated cellular programming" (IMCP). This term is intended to more broadly refer to an antibody-mediated cellular programming effect, however for simplicity reference is made to the IVIg example, and hence IMCP is used throughout without prejudice. It is not intended to restrict the effect to only IVIg treatment regimes.

Figure 8:
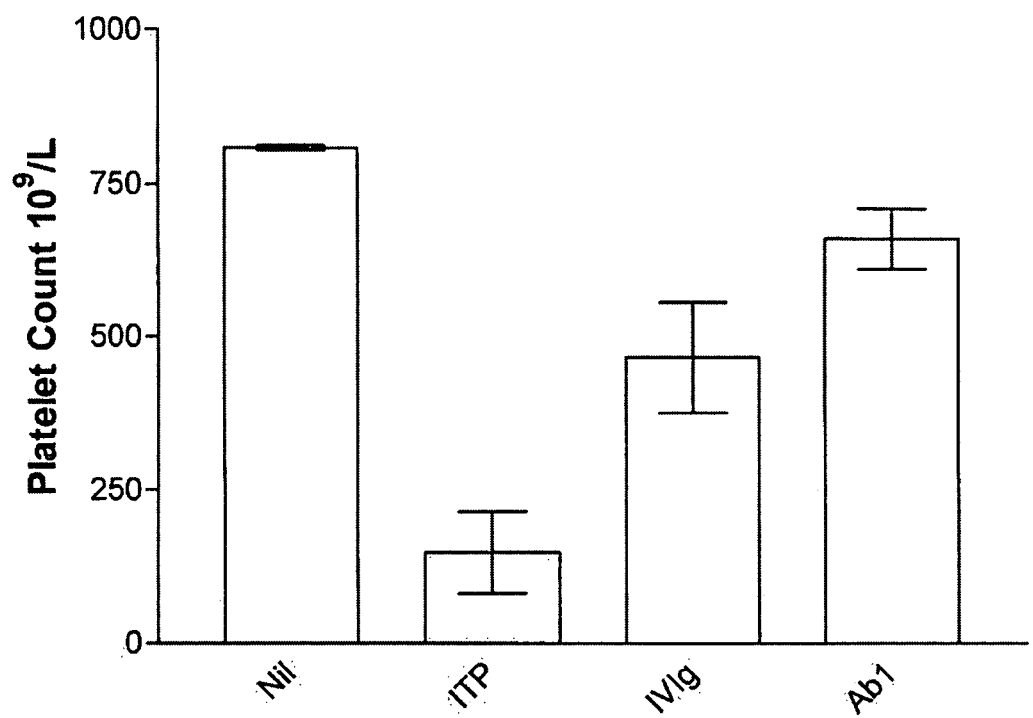
FIG. 8 is a graphical representation illustrating IMCP-like effects as shown by IVIg and anti-CD44 treatment regimes.

A monoclonal antibody (anti-CD44) is also demonstrated to inhibit immune thrombocytopenia by the same mechanism (ie. an IMCP-like effect in FIG. 8. Here, anti-CD44+ leukocytes were incubated for 30 min, unbound anti-CD44 washed off, leukocytes were then injected into ITP mice, and an amelioration of thrombocytopenia resulted. Mice in the first column (Nil) were uninjected. Mice in the second column (ITP) were treated with anti-platelet antibody (αCD41) only. On Day 1, mice in the third and fourth column (IMCP) were injected intravenously with splenic leukocytes ($10^6$/mouse) that went through the IMCP process with IVIg or anti-CD44 for 30 min. On Day 2 mice in columns (second to fourth) were injected with 2 µg anti-platelet antibody. On Day 3, all mice were bled for platelet enumeration as described (Blood 105: 1546-1548, 2005).

Figure 9:
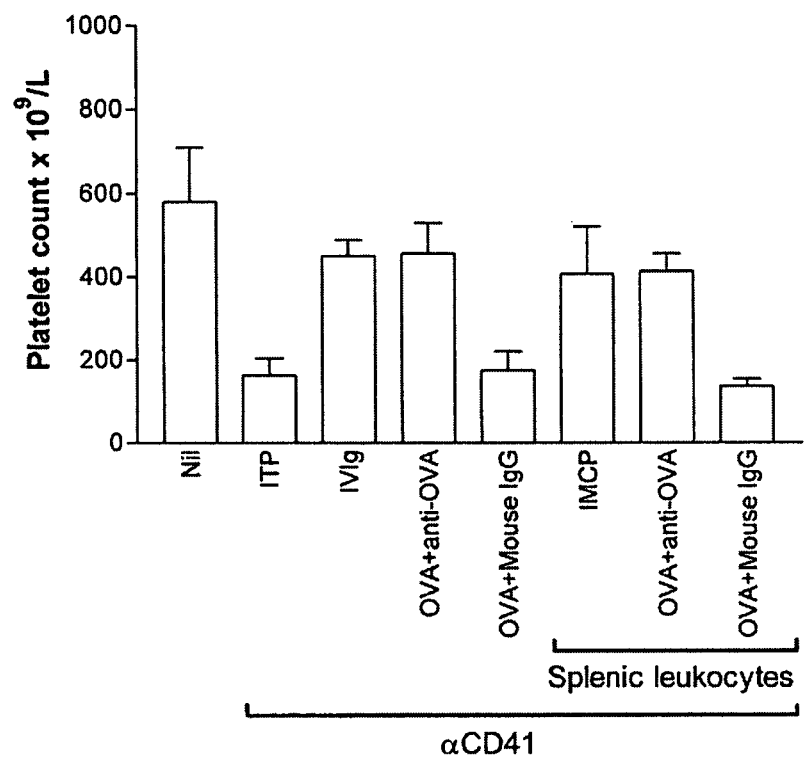
FIG. 9 is a graphical representation illustrating IMCP-like effects as shown by IVIg and soluble antigen-specific antibody treatment regimes.

FIG. 9 illustrates an antibody-mediated cellular programming effect, herein referred to as IMCP, as mentioned above, at work in splenic leukocytes incubated with monoclonal anti-OVA, thus establishing a basis for the mode of action of the treatment regimes of the present invention. As illustrated, anti-ovalbumin+ovalbumin+leukocytes are incubated for 30 min, unbound anti-ovalbumin and ovalbumin are washed off, and leukocytes are injected into ITP mice to provide ameliorating effect against thrombocytopenia in vivo. According to FIG. 9, mice in the first column (Nil) were uninjected. Mice in the second column (ITP) were treated with anti-platelet antibody (αCD41) only. On Day 1, mice in the third column (IVIg) were injected with 50 mg/ml of dialyzed IVIg. Mice in the fourth column were injected (i.v.) with 1 mg OVA that had been pre-incubated with 50 μg of monoclonal anti-OVA (IgG1, clone OVA-14 Sigma). Mice in the fifth column were treated as in fourth column except with control mouse IgG (mouse IgG, Cat#10400, Caltag) in place of monoclonal anti-OVA. Mice in the sixth column (IMCP) were injected intravenously with splenic leukocytes ($10^6$/mouse) that went through the IMCP process with dialyzed IVIg for 30 min. Mice in the seventh column were treated with splenic leukocytes ($10^6$/mouse) that went through IMCP process with 1 mg OVA that had been pre-incubated with 50 μg of monoclonal anti-OVA for 30 min. Mice in the eighth column were treated as in seventh column except with control mouse IgG in place of monoclonal-anti-OVA. On Day 2, mice in columns (second to eighth) were injected with 2 μg anti-platelet antibody. On Day 3, all mice were bled for platelet enumeration as described (Blood 102:558-560, 2003).

Figure 13:
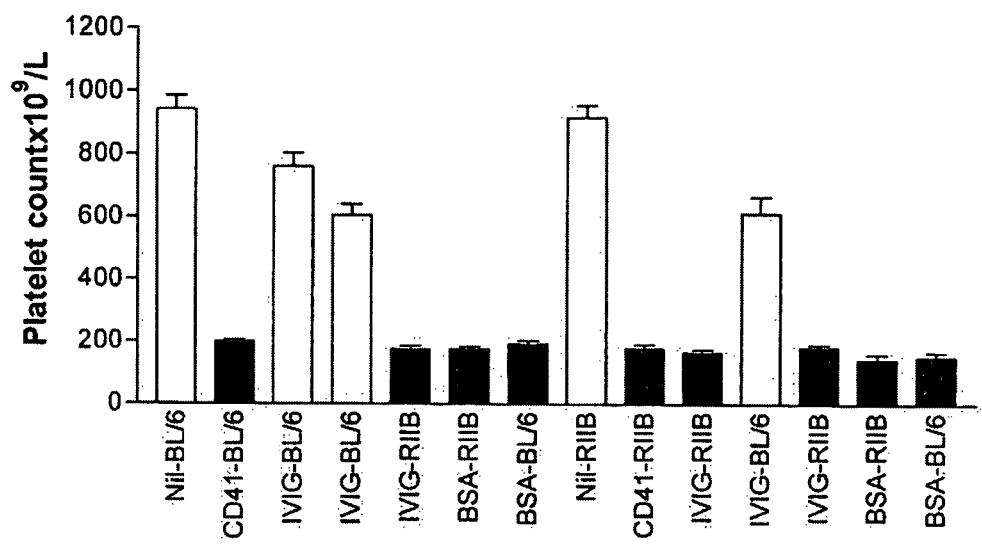
FIG. 13 is a graphical representation illustrating that IVIg-treated leukocytes show therapeutic potential in the absence of Fcγ RIIB expression.

IVIg, anti-CD44 (KM-114), and antibody to soluble antigens (in the presence of the soluble antigen) cannot ameliorate thrombocytopenia in mice which are genetically deficient in the inhibitory Fcγ receptor (FcγRIIB) Interestingly, however, we show here that these same antibodies can all ameliorate thrombocytopenia when they are pre-incubated with leukocytes isolated from mice that are genetically deficient in FcγRIIB (FcγRIIB$^{-/-}$) and the FcγRIIB$^{-/-}$ leukocytes are injected into wild type mice. Thus, the IMCP effect as herein reported can work where leukocytes do not express an FcγRIIB receptor. However, FcγRIIB receptor expression was required in the recipient in order to achieve IMCP. In the reverse of this experiment (where the leukocytes are from FcγRIIB$^{+/+}$ mice and the recipient mice are FcγRIIB$^{-/-}$), again, IVIg, anti-CD44, and anti-soluble antigen (+the antigen) all cannot ameliorate the thrombocytopenia (FIG. 13). As shown in FIG. 13, mice in the $1^{st}$ column (Nil-BL/6) are uninjected C57BL/6 mice. Mice in the $2^{nd}$ column (CD41-BL/6) were C57BL/6 mice treated with anti-platelet antibody (αCD41) only. Mice in the $8^{th}$ column (Nil-RIIB) were uninjected FcγRIIB$^{-/-}$ mice. Mice in the $9^{th}$ column (CD41-RIIB) were FcγRIIB$^{-/-}$ mice treated with anti-platelet antibody (αCD41) only. On Day 1, mice in the $3^{rd}$ column (IVIG-BL/6) were injected with 50 mg/ml IVIg. Mice in the fourth column (IVIG-BL/6) were C57BL/6 mice injected intravenously with splenic leukocytes ($10^6$/mouse) from C57BL/6 mice that went through the IMCP process with IVIg for 30 min. Mice in the $5^{th}$ column (IVIG-RIIB) were FcγRIIB$^{-/-}$ mice injected intravenously with splenic leukocytes ($10^6$/mouse) from C57BL/6 mice that went through the IMCP process with IVIg for 30 min. Mice in the $6^{th}$ column (BSA-RIIB) were FcγRIIB$^{-/-}$ mice injected intravenously with splenic leukocytes ($10^6$/mouse) from C57BL/6 mice that went through the IMCP process with BSA for 30 min. Mice in the $7^{th}$ column (BSA-BL/6) were C57BL/6 mice injected intravenously with splenic leukocytes ($10^6$/mouse) from C57BL/6 mice that went through the IMCP process with BSA for 30 min. Mice in the $10^{th}$ column (IVIG-RIIB) were injected with 50 mg/ml IVIg. Mice in the $11^{th}$ column (IVIG-BL/6) were C57BL/6 mice injected intravenously with splenic leukocytes ($10^6$/mouse) from FcγRIIB$^{-/-}$ mice that went through the IMCP process with IVIg for 30 min. Mice in the $12^{th}$ column (IVIG-RIIB) were FcγRIIB$^{-/-}$ mice injected intravenously with splenic leukocytes ($10^6$/mouse) from FcγRIIB$^{-/-}$ mice that went through the IMCP process with IVIg for 30 min. Mice in the $13^{th}$ column (BSA-RIIB) were FcγRIIB$^{-/-}$ mice injected intravenously with splenic leukocytes ($10^6$/mouse) from FcγRIIB$^{-/-}$ mice that went through the IMCP process with BSA for 30 min. Mice in the $14^{th}$ column (BSA-RIIB) were C57BL/6 mice injected intravenously with splenic leukocytes ($10^6$/mouse) from FcγRIIB$^{-/-}$ mice that went through the IMCP process with BSA for 30 min. On Day 2, mice in columns ($2^{nd}$ to $7^{th}$ and $9^{th}$ to $14^{th}$, inclusive) were injected with 2 μg anti-platelet antibody. On Day 3, all mice were bled for platelet enumeration as described in Blood 102:558-560, 2003 with the exception that mice were bled by the saphenous vein in accordance with this embodiment of the present invention.

It is therefore concluded that IVIg, anti-CD44, and anti-soluble antigen (in the presence of the antigen) do not function by binding to the FcγRIIB on the leukocyte but do all function by a highly related mechanism, which we refer to as an IVIg-mediated cellular programming mechanism, or IMCP. Furthermore, the cellular programming mechanism (IMCP) of the present invention establishes an underlying mode of action for antibody-based treatment regimes of the present invention that appears to be more accurate than the previously reported RES blockade mechanism.

It will be appreciated by persons skilled in the art that other antigens and antibodies could also be used according to the above described method to achieve similar results. It will also be appreciated that the method and composition can be applied to mammals other than mice and rabbits, and particularly in humans.

The embodiment(s) of the invention described above is(are) intended to be exemplary only. The scope of the invention is therefore intended to be limited solely by the scope of the appended claims.

REFERENCES AND NOTES

1. P. Bruhns, A. Samuelsson, J. W. Pollard, J. V. Ravetch, *Immunity* 18, 573-81 (April, 2003).
2. A. Samuelsson, T. L. Towers, J. V. Ravetch, *Science* 291, 484-6. (2001).
3. A. R. Crow et al., *Blood* 102, 558-560 (Jul. 15, 2003).
4. S. Akilesh et al., *J Clin Invest* 113, 1328-33 (May, 2004).
5. V. L. Ott, D. C. Fong, J. C. Cambier, *J Allergy Clin Immunol* 108, S95-8. (2001).
6. B. A. Binstadt, R. S. Geha, F. A. Bonilla, *J Allergy Clin Immunol* 111, 697-703 (April, 2003).
7. X. Cao et al., *J Immunol* 172, 4851-7 (Apr. 15, 2004).
8. S. Latour, C. Bonnerot, W. H. Fridman, M. Daeron, *J Immunol* 149, 2155-62 (Sep. 15, 1992).
9. B. De Andres et al., *J Immunol* 146, 1566-70 (Mar. 1, 1991).
10. T. Takai, *Immunology* 115, 433-40 (August, 2005).
11. J. F. Timms et al., *Mol Cell Biol* 18, 3838-50 (July 1998).
12. F. Nimmerjahn, P. Bruhns, K. Horiuchi, J. V. Ravetch, *Immunity* 23, 41-51 (July, 2005).
13. V. Siragam et al., *J Clin Invest* 115, 155-60 (January, 2005).
14. R. Clynes, *J Clin Invest* 115, 25-7 (January, 2005).
15. C57BL/6 and BALB/c mice (female 6 to 8 weeks of age) were purchased from Jackson Laboratory, FcγRIIB$^{-/-}$ (B6; 129S4-Fcγr2b$^{tm1Rav}$/J) mice were purchased from Jackson Laboratory and bred in our facility. Severe combined immune deficient (CB17/lcr-Prkdc$^{scid}$/Crl) virgin mice were purchased from Charles River Laboratories. FcRγ$^{-/-}$ (B6.129P2-Fcer1g$^{tm1Rav}$) mice were from Taconic Laboratory. All mice were housed in the St. Michael's Hospital Research Vivarium, and SCID mice were housed under gnotobiotic conditions. All methods involving animals have been approved by the Animal Care Committee of St. Michael's Hospital, Toronto. IVIg was Gamimune N, 10%

(Bayer Corporation). Normal rat IgG and Goat (Fab')$_2$ anti-rat IgG were purchased from Caltag. Rat anti-mouse PIR-A/B was from BD PharMingen. BSA was from Sigma and was dissolved in 0.2 M Glycine (pH 4.25). In experiments where IVIg and BSA were used to prime leukocytes, these protein solutions were dialysed in phosphate-buffered saline (PBS), pH 7.2 to gradually neutralize the pH.

16. Spleens from appropriate mice were removed, mechanically disrupted in 5 ml of RPMI-1640 medium (Sigma), supplemented with 10% heat-inactivated fetal calf serum, 80 mg/ml streptomycin sulphate, 0.2 mg/ml a amphotericin and then filtered through a 70-mm nylon mesh strainer. Erythrocytes were lysed using 0.15 M $NH_4Cl$, 10 mM $KHCO_3$, 0.1 mM $Na_2$ EDTA (ACK) lysis buffer and washed 2× in RPMI-1640. The cells ($1.4×10^6$/ml) were incubated with 18 mg/ml dialyzed IVIg or BSA and for 30 min at 37° C., washed 2× in RPMI-1640, resuspended to $5×10^6$/ml and injected (200 µl) into the tail vein of recipient mice. In the anti-FcγRIIIA and PIR-A/B experiments, leukocytes ($2×10^7$/ml and $4×10^6$/ml, respectively) were first treated with antibody 2.4G2 (2.5 µg/ml), 6C1 (10 µg/ml), or normal rat IgG for 15 min at 22° C. The cells were then washed, reacted with goat (Fab')$_2$ anti-rat IgG (25 µg/ml) for 30 min at 37° C., washed 2× in RPMI-1640, resuspended to $5×10^6$/ml and injected (200 µl) into the tail vein of recipient mice. In the immune complex experiments, leukocytes were first treated with soluble immune complexes or a control protein preparation for 30 min at 37° C., the cells washed and injected (200 µl) into the tail vein of recipient mice. The immune complexes were made by incubating 1 mg of ovalbumin with 50 µg monoclonal anti-ovalbumin (Clone OVA-14, antibody subclass IgG1, Sigma) for 30 min at 22° C. The immune complex control preparation was made by incubating 1 mg of ovalbumin with 50 mg normal mouse IgG for 30 min at 22° C.

17. For the administration of IVIg (Gamimune N, 10%, Bayer Corporation), BSA (Sigma), or IVIg-primed leukocytes, mice were first injected intraperitoneally with 50 mg of IVIg, BSA (~equivalent to 2 g/kg body weight), or the indicated number of IVIg-primed cells. After 24 hrs, mice were rendered thrombocytopenic by the intraperitoneal injection of 2 µg anti-CD41 (anti-integrin IIb) antibody in 200 µL PBS. Twenty-four hours later, mice were bled by the saphenous vein and the platelets were counted on a flow rate-calibrated FACScan flow cytometer (Becton Dickinson) as previously described in detail (13, 18-19).

18. A. R. Crow, S. Song, J. W. Semple, J. Freedman, A. H. Lazarus, *Br J Haematol* 115, 679-86. (2001).

19. S. Song, A. R. Crow, J. Freedman, A. H. Lazarus, *Blood* 101, 3708-13 (May 1, 2003).

The teachings of the above listed references are herein incorporated by reference.

The embodiment(s) of the invention described above is(are) intended to be exemplary only. The scope of the invention is therefore intended to be limited solely by the scope of the appended claims.

We claim:

1. A method for treating an immune thrombocytopenia or inflammatory arthritis in a mammal, said method comprising:
    a) obtaining a sample of leukocytes having a Fcγ receptor and being syngeneic or autologous to the cells of the treated mammal;
    b) contacting said leukocytes of step a) with an antibody composition binding to a γ-chain dependent Fcγ receptor under conditions sufficient to allow the crosslinking of the γ-chain dependent Fcγ receptor; and
    c) administering said leukocytes of step b) to said mammal; wherein said treated leukocytes ameliorate said immune thrombocytopenia or inflammatory arthritis in said mammal;
    wherein the antibody composition is selected from the group consisting of i) an IVIg, ii) a combination of an antibody specific for the FcγRIIIA receptor and an anti-IgG antibody, and iii) an immune complex comprising an antigen and an IgG antibody specific for the antigen.

2. The method of claim 1, wherein said leukocytes are obtained by separating leukocytes from whole blood taken from said mammal and/or from a healthy mammal.

3. The method of claim 1, wherein said leukocytes comprise dendritic cells purified from leukocytes obtained from said mammal and/or a healthy mammal.

4. The method of claim 1, wherein said leukocytes comprise dendritic cells cultured from a feed stock of leukocytes.

5. The method of claim 1, wherein said leukocytes comprise dendritic cells generated from $CD14^+$ monocytes obtained from said mammal and/or a healthy mammal.

6. The method of claim 1, wherein said antibody composition comprises a combination of 2.4G2 antibody (ATCC Catalog No. HB-197) and an anti-IgG antibody.

7. The method of claim 1, wherein said immune complex is a complex of ovalbumin and an anti-ovalbumin antibody.

* * * * *